US008617895B2

(12) United States Patent
Fox et al.

(10) Patent No.: US 8,617,895 B2
(45) Date of Patent: Dec. 31, 2013

(54) POLYCATIONIC QUATERNARY AMMONIUM POLYMER COATINGS FOR IMMOBILIZING BIOLOGICAL SAMPLES

(75) Inventors: William Alan Fox, Burlington, NC (US); William Carl Ray, III, Durham, NC (US)

(73) Assignee: Tripath Imaging, Inc., Burlington, NC (US)

( * ) Notice: Subject to any disclaimer, the term of this patent is extended or adjusted under 35 U.S.C. 154(b) by 356 days.

(21) Appl. No.: 11/233,496

(22) Filed: Sep. 22, 2005

(65) Prior Publication Data

US 2006/0073510 A1  Apr. 6, 2006

Related U.S. Application Data

(60) Provisional application No. 60/612,391, filed on Sep. 23, 2004.

(51) Int. Cl.
*G01N 31/00* (2006.01)
*G01N 33/00* (2006.01)

(52) U.S. Cl.
USPC .................................. 436/8; 436/18; 436/111

(58) Field of Classification Search
None
See application file for complete search history.

(56) References Cited

U.S. PATENT DOCUMENTS

| | | | |
|---|---|---|---|
| 5,330,911 A | 7/1994 | Hubbell et al. | |
| 5,346,831 A | 9/1994 | Carrico, Jr. et al. | |
| 5,403,882 A * | 4/1995 | Huggins | 524/406 |
| 5,419,279 A | 5/1995 | Carrico, Jr. et al. | |
| 5,459,080 A * | 10/1995 | Adamczyk et al. | 436/538 |
| 5,716,709 A | 2/1998 | Ferguson et al. | |
| 5,922,531 A | 7/1999 | Dubin et al. | |
| 6,025,059 A | 2/2000 | McGee et al. | |
| 6,127,448 A | 10/2000 | Domb | |
| 6,447,887 B1 * | 9/2002 | Claus et al. | 428/209 |
| 6,649,343 B1 | 11/2003 | Hirota et al. | |
| 6,657,003 B2 | 12/2003 | Fox | |
| 6,673,629 B2 | 1/2004 | Yoshimura et al. | |
| 6,689,478 B2 | 2/2004 | Laguitton | |
| 6,710,111 B2 | 3/2004 | Kuo et al. | |
| 6,713,255 B1 | 3/2004 | Makino et al. | |
| 6,783,838 B2 | 8/2004 | Coleman et al. | |
| 6,808,742 B2 | 10/2004 | Rouse et al. | |
| 2001/0039014 A1 | 11/2001 | Bass et al. | |
| 2002/0037383 A1 | 3/2002 | Spillman, Jr. et al. | |
| 2002/0050220 A1 * | 5/2002 | Schueller et al. | 101/486 |
| 2002/0160367 A1 * | 10/2002 | Coleman et al. | 435/6 |
| 2003/0013124 A1 * | 1/2003 | Kuo et al. | 435/7.1 |
| 2003/0021982 A1 | 1/2003 | Kotov | |
| 2003/0054383 A1 | 3/2003 | Bass et al. | |
| 2003/0054384 A1 | 3/2003 | Bass et al. | |
| 2003/0064393 A1 | 4/2003 | Bass et al. | |
| 2003/0211129 A1 | 11/2003 | Spillman, Jr. et al. | |
| 2003/0219909 A1 * | 11/2003 | Lally et al. | 436/518 |
| 2004/0013638 A1 | 1/2004 | Aubay et al. | |
| 2004/0029143 A1 | 2/2004 | Van Ness et al. | |
| 2004/0031712 A1 | 2/2004 | Maxim et al. | |
| 2004/0086709 A1 * | 5/2004 | Hammond Cunningham et al. | 428/335 |
| 2004/0121334 A1 | 6/2004 | Wei et al. | |
| 2004/0121339 A1 | 6/2004 | Zhou et al. | |
| 2004/0151930 A1 | 8/2004 | Rouns et al. | |
| 2004/0162405 A1 | 8/2004 | Braun et al. | |
| 2004/0182533 A1 | 9/2004 | Blum et al. | |
| 2004/0185284 A1 | 9/2004 | Ho et al. | |
| 2004/0202774 A1 | 10/2004 | Chudzik et al. | |
| 2004/0203149 A1 | 10/2004 | Childs et al. | |
| 2005/0059150 A1 * | 3/2005 | Guarino et al. | 435/370 |
| 2005/0153071 A1 * | 7/2005 | Bouvrette et al. | 427/212 |

FOREIGN PATENT DOCUMENTS

| | | |
|---|---|---|
| EP | 124676 A1 * | 11/1984 |
| JP | 11-014909 | 1/2009 |
| WO | WO-03/035278 A1 | 5/2003 |

OTHER PUBLICATIONS

Wang et al., Electrochemistry and electrocatalysis with myoglobin in biomembrane-like DHP-PDDA polyelectrolyte-surfactant complex films, 2001, J Colloid Interface Sc 236: pp. 166-172.*

Li, Mengyan, et al., "Fabrication of 3-D Gelatin-Patterned Glass Substrates With Layer-by-Layer and Lift-Off (LbL-LO) Technology," *IEEE Transactions on Nanotechnology*, 2004, vol. 3(1), pp. 115-123.

Mohammed, J. Shaikh, et al., "Micropatterning of Nanoengineered Surfaces to Study Neuronal Cell Attachment in Vitro," *Biomacromolecules*, 2004, vol. 5, pp. 1745-1755.

He, P., et al., Assembly of Electroactive Layer-by-Layer Films of Hemoglobin and Polycationic Poly(diallyldimethylammonium), *Biomacromolecules*, 2002, pp. 139-146, vol. 3.

"Advanced Functional Materials Research Section," Institute of Advanced Energy, Kyoto University, posted online (http://www.iae.kyoto-u.ac.jp/press/AR/AR-96/AFM.html).

(Continued)

*Primary Examiner* — Shafiqul Haq
*Assistant Examiner* — Gary E Hollinden
(74) *Attorney, Agent, or Firm* — Alston & Bird LLP

(57) ABSTRACT

The present invention is directed to a pre-coated substrate, such as a slide, that is useful for immobilizing a sample. The invention is further provides methods of preparing such pre-coated substrates and methods of analyzing biological samples immobilized on such pre-coated substrate. The substrate is coated with a polycationic polymeric coating material specifically selected such that that coated substrate exhibits increased stability and prolonged shelf-life. Preferred polymeric coating materials include allylic or vinylic polymers having cationic groups thereon and having no more than a small percentage of peptidic monomeric linkages, particularly polydiallyldimethylammonium (PDDA).

41 Claims, No Drawings

(56) References Cited

OTHER PUBLICATIONS

Ai, et al., "Electrostatic Layer-by-Layer Nanoassembly on Biological Microtemplates: Platelets," *Biomacromolecules*, 2002, vol. 3, pp. 560-564.

Bertrand, et al., "Ultrathin Polymer Coatings by Complexation of Polyelectrolytes at Interfaces: Suitable Materials, Structure and Properties," *Macromol. Rapid Commun.*, 2000, vol. 21(7), pp. 319-348.

"Biomaterials—an Offer the Body Can't Reject," Virginia Tech Research Magazine, posted online Winter 2003 (http://www.research.vt.edu/resmag/2003winter/biomaterials.html).

Brynda, et al., "Interaction of Blood Plasma with Immobilized Protein Assemblies," *40th Microsymposium: Polymers in Medicine*, Jul. 17-20, 2000, Prague, Czech Republic, Poster No. P35.

Chang-Yen, et al., "A Novel Integrated Optical Dissolved Oxygen Sensor for Cell Culture and Micro Total Analysis Systems," *2002 Annual MEMS Conference*, Jan. 25, 2002, San Jose, California.

Cheng, et al., "Electrostatic Self Assembly of Nanocomposite Polymers in Grating Structures,"*J. Vac. Sci. Technol. B*, 2001, vol. 19(6), pp. 2736-2740.

Cras, et al., "Comparison of Chemical Cleaning Methods of Glass in Preparation for Silanization,"*Biosens. Bioelectron.*, 1999, vol. 14, pp. 683-688.

Friedl, et al., "Studies on a New Human Cell Line (SiHa) Derived from Carcinoma of Uterus. I. Its Establishment and Morphology," *Proc. Soc. Exp. Biol. Med.*, 1970, vol. 135, pp. 543-545.

Gorman, "Layered Approach: a Simple Technique for Making Thin Coatings is Poised to Shift from Curiosity to Commodity," *Science News Online*, vol. 164(6), Aug. 9, 2003, p. 91.

Hou, et al., "Covalent Attachment of Deoxyribonucleic Acid (DNA) to Diazo-Resin (DAR) in Self-Assembled Multilayer Films," *Polymer Bulletin*, 2002, vol. 47, pp. 445-450.

Lerche, et al., "Microcontainers (LUMiTainers) for Preparation of Biological Objects for Electron Microscopy and Cell Biology Processing, Product Characterisation and Application," *Proceedings of the Fifth International Workshop on Bioencapsulation*, Sep. 23-26, 1996, Potsdam, Germany.

"Measurement of Layer-by-Layer Self-Assembly Film Using RAS-8000 Grazing Angle Specular Reflectance Accessory," Shimadzu Application News, No. A325, posted online (http://www.shimadzu.com.br/analitica/aplicacoes/espectrofotometros/ftir/la103-e005.pdf).

"New DNA Chip Could Speed Drug and Genetic Screening," UniScience News Net, Inc., posted online Oct. 29, 2001 (http://unisci.com/stories/20014/1029014.htm).

Sakai, et al., "Mixed Ternary Ion Associate Formation between Xanthene Dye, Cinchona-Alkaloid and Quaternary Ammonium Ion and Its Application to the Determination of Trace Amounts of Quaternary Ammonium Salts in Pharmaceuticals," *Talanta*, 2003, vol. 59, pp. 167-175.

Seyfert, et al., "Adhesion of Leucocytes to Microscope Slides as Influenced by Electrostatic Interaction," *Biomaterials*, 1995, vol. 16(3), pp. 201-207.

Stuart, et al., "Adsorbed Polymer Layers in Nonequilibrium Situations,"*Annu. Rev. Mater. Sci.*, 1996, vol. 26, pp. 463-500.

Tartakovsky, et al., "The Adsorption of Cationic and Amphoteric Copolymers on Glass Surfaces: Zeta Potential Measurements, Adsorption Isotherm Determination, and FT Raman Characterization," *J. Colloid Interface Sci.*, 2003, vol. 263, pp. 408-419.

Wang, et al., "Protein Binding on Polyelectrolyte-Treated Glass Effect of Structure of Adsorbed Polyelectrolyte," *J. Chromatogr. A*, 1998, vol. 808, pp. 61-70.

Zhou, et al., "A Novel DNA Immobilization Technique to Fabricate DNA Chips," *2001 Joint International Meeting—The 200th Meeting of the Electrochemical Society, Inc. and the 52nd Annual Meeting of the International Society of Electrochemistry*, San Francisco, California, Sep. 2-7, 2001.

Zhou, et al., "Spectral and Electrochemical Characterization of Immobilization of DNA onto the Self-Assembling Polyelectrolyte Film on the Gold Surface," *2001 Joint International Meeting—The 200th Meeting of the Electrochemical Society. Inc. and the 52nd Annual Meeting of the International Society of Electrochemistry*, San Francisco, California, Sep. 2-7, 2001.

Zhou, et al., "Toxicity Screening by Electrochemical Detection of DNA Damage by Metabolites Generated In Situ in Ultrathin DNA—Enzyme Films," *J. Am. Chem. Soc.*, 2003, vol. 125, pp. 1431-1436.

Lei et al., "Supramolecular Assembly of Porphyrin Bound DNA and Its Catalytic Behavior for Nitric Oxide Reduction," *Electrochimica Acta*, 2004, vol. 49, pp. 2453-2460.

Pei et al., "Assembly of Alternating Polycation and DNA Multilayer Films by Electrostatic Layer-by-Layer Adsorption," *Biomacromolecules*, 2001, vol. 2, pp. 463-468.

Watts, "The Use of Cationic Polyelectrolytes in the Preparation of Cell Monolayers for Automated Cell Scanning and Diagnostic Cytopathology," *The International Academy of Cytolology*, 1984, pp. 272-278, vol. 6, No. 4.

Wenjiang, L., et al., "Alternate deposition of horseradish peroxidase and bipolar pyridine salt on the solid surface to prepare electrocatalytically active enzyme thin film," *Thin Solid Films*, 2001, vol. 386, pp. 121-126.

\* cited by examiner

POLYCATIONIC QUATERNARY AMMONIUM POLYMER COATINGS FOR IMMOBILIZING BIOLOGICAL SAMPLES

CROSS-REFERENCE TO RELATED APPLICATION

This application claims the benefit of U.S. Provisional Application No. 60/612,391, filed Sep. 23, 2004, which is incorporated by reference herein in its entirety.

FIELD OF THE INVENTION

The present invention is directed to a method for preparing a coated substrate for immobilizing a biological sample thereon, preferentially for analysis thereof. The present invention is further directed to a pre-coated substrate prepared according to the above method. The substrate is coated with a polycationic polymer providing a stable polymer layer capable of ionic interaction with anionic biological components.

BACKGROUND

Various biological preparatory techniques require immobilization of sample materials, such as cells, tissue, proteins, or nucleic acids, to a substrate prior to subsequent processing. Many of these biological materials of interest are anionic in nature, exhibiting net negative charge sites. One method of immobilizing these materials is to coat the target substrate with a chemical solution containing active ingredients that are cationic in nature, exhibiting a net positive charge. As the biological materials of interest to be immobilized exhibit net negative charge sites, the biological materials bind to the surface of the substrate through interaction with the net positive charge sites of the coating solution. This adhesion property of the coating solution allows the immobilization of sample material for subsequent processing.

The immobilization effect described above can be created through the use of coatings containing various active ingredients currently known in the art. For example, it is currently known to use coating agents, such as poly-1-lysine, 3-aminopropyl triethoxysilane, chrome alum gelatin, and egg white albumin. One of the most widely used of these known immobilization agents is poly-1-lysine (PLL).

PLL is a large polycationic homopolymer that exhibits a strong positive charge produced by the terminal amino groups of the lysine residue side chains all along the polymer. L-Lysine [(S)-2,6-diaminohexanoic acid] is an amino acid of the chemical structure shown below in formula (1).

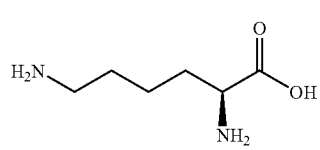

(1)

The polymer PLL is a chain of 1-lysine monomer units attached through peptide bonds. The chemical structure for PLL is provided below in formula (2), wherein n is an integer representing the number of monomer units in the polymer chain.

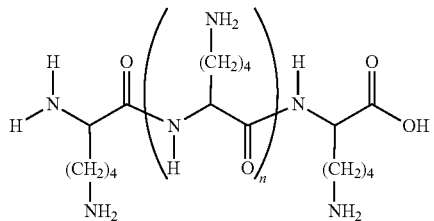

(2)

While PLL is widely used as a polycationic polymer coating, substrates coated with PLL tend to lose their immobilization effectiveness over a relatively short time period. This decline in effectiveness over time is generally thought to be due to oxidation of the PLL side chain amine groups. The oxidized groups do not exhibit the net positive charge required for proper adhesion to the biological materials to be immobilized.

The effectiveness of PLL as an immobilization agent is also limited by its inherent chemical structure shown above in formula (2). As previously noted, the amino acid residues of the polymer are connected by peptide bonds (—CO—NH— bonds). These peptide bonds are highly vulnerable to cleavage by proteolytic enzymes, such as trypsin, and to general hydrolytic cleavage, such as through attack from a nucleophilic substance. Cleavage of the peptide bonds results in PLL molecules of substantially shorter chain length, as measured by the average molecular weight of the polymer. As the molecular weight of the PLL molecule is reduced through proteolytic cleavage, the immobilization capability of the molecule (i.e., its adhesive property) becomes greatly reduced.

Known immobilization agents, such as PLL, exhibit limited usefulness as a result of the chemical instabilities described above. Accordingly, substrates coated with the known agents also exhibit limited usefulness, particularly for long-term use or use after significant storage time. Given the limited stability of substrates coated with the known immobilization agents, it would be highly useful to have a pre-coated substrate that is coated with an immobilization agent that exhibits increased stability, particularly being useful for immobilizing a biological sample for observation.

SUMMARY OF THE INVENTION

The present invention provides a coated substrate preferentially adapted for immobilizing a biological sample. The substrate is coated with a polycationic polymer exhibiting increased stability in comparison to the immobilization agents previously known in the art. Accordingly, the substrate coated with the stable polycationic polymer is useful for immobilizing biological samples having net a negative charge, and the coated substrate maintains such usefulness for an extended time period.

In one embodiment of the present invention, there is provided a method for preparing a coated substrate. Preferentially, the coated substrate is adapted for immobilizing a biological sample. According to one embodiment, the method comprises providing a substrate having a surface comprising a plurality of anionic groups, and contacting the substrate with a composition comprising a solution of a non-peptidic polymeric material to form a coating of the non-peptidic polymeric material on at least a portion of the surface of the substrate. The solution comprising the non-peptidic polymeric material can be an aqueous solution or an organic solution, preferably having a pH of at least about 6.

In one preferred embodiment of the invention, the method further comprises the steps of drying the substrate coated with the non-peptidic polymeric material. Preferentially, the coated substrate with the dried non-peptidic polymeric material thereon is rinsed.

In another preferred embodiment of the invention, the method is characterized by the absence of substrate cleaning. In particular, the method excludes subjecting the substrate to a cleaning process prior to contacting the substrate with the non-peptidic polymeric material.

According to another aspect of the present invention, there is provided a pre-coated substrate, such as a microscope slide, that is preferentially adapted for immobilizing a biological sample for analysis. According to one embodiment, the substrate comprises a surface having a plurality of anionic groups for providing a net negative charge, and the substrate is coated with a non-peptidic polymeric material comprising a plurality of cationic groups.

The pre-coated substrate, according to this aspect of the invention, is characterized by its capability of immobilizing an average number of cells per surface area of the substrate. In one particular embodiment, the pre-coated substrate is capable of immobilizing an average number of cells per surface area of at least about 20,000 cells/cm$^2$ when the pre-coated substrate is contacted with 1 mL of a suspension of cells from the SiHa cell line.

According to another embodiment of the invention, the non-peptidic polymeric material used for coating the pre-coated substrate comprises an allylic polymer, a vinylic polymer, or a combination thereof, preferentially comprising cationic groups selected from the group consisting of primary amines, secondary amines, tertiary amines, and quaternary amines. In one preferred embodiment, the non-peptidic polymeric material comprises polydiallyldimethylammonium (PDDA). In another preferred embodiment of the invention, the non-peptidic polymeric material comprises polyallylamine (PAH).

The substrate according to the present invention can be any item or apparatus useful or necessary for observing or analyzing a biological material. In one preferred embodiment, the substrate is selected from the group consisting of slides, plates, beads, test tubes, cuvettes, dipsticks, swabs, and gauze. In a further embodiment, the substrate could be a device useful as a contaminant gathering device. For example, the substrate could be a glove, a towel, or a medical drape.

The coated substrates according to the present invention are adapted for immobilizing materials that are at least partially anionic in nature. Preferably, the materials for immobilization have a net negative charge. Accordingly, the coated substrates are useful for immobilizing various materials, particularly being adapted for immobilizing biological material, such as cells, tissue, fluids, DNA, RNA, proteins, and similar biological material having anionic groups available for interaction with the cationic groups of the non-peptidic polymeric material used in preparing the coated substrate of the present invention.

According to another aspect of the present invention, there is provided a method of analyzing a biological sample. In one embodiment according to this aspect of the invention, the method comprises the following steps: providing a pre-coated substrate adapted for immobilizing a biological sample, the substrate comprising a surface having a plurality of anionic groups, wherein the substrate is coated with a non-peptidic polymeric material comprising a plurality of cationic groups; applying a biological sample to the pre-coated substrate to immobilize the biological sample on the substrate; and analyzing the biological sample immobilized on the pre-coated substrate. In a particular embodiment, the pre-coated substrate is capable of immobilizing an average number of cells per surface area of at least about 20,000 cells/cm$^2$ when the pre-coated substrate is contacted with 1 mL of a suspension of cells from the SiHa cell line.

DETAILED DESCRIPTION OF THE INVENTION

The present invention now will be described more fully hereinafter. However, this invention may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise.

The pre-coated substrate of the present invention is characterized by the use of a polymeric coating material preferably demonstrating immobilization capabilities at least equivalent to the coating agents presently known, but also demonstrating extended stability of this immobilization effect after coating of the substrate. Further, in a preferred embodiment, the polymeric coating material is of a chemical structure that is less vulnerable, or invulnerable, to proteolytic or hydrolytic degradation as compared to conventional coating agents, such as PLL.

The polymeric coating material according to the present invention comprises a plurality of cationic groups that are available for interaction with anionic groups, such as on a substrate to be coated and within a biological sample to be immobilized. The cationic groups can be an integral component of the polymeric backbone of the polymeric coating material or present as side chain groups. The cationic groups can be any group having a net positive charge and being capable of ionic interaction with oppositely charged particles or groups. Particularly preferred cationic groups include amine groups and ammonium groups, which can be primary, secondary, tertiary, or quaternary amine groups or ammonium groups. Cationic groups, particularly an ammonium group, often have a negatively charged counterion associated with the group, such as chloride.

Cationic groups exhibiting greater degrees of substitution are particularly preferred. As previously noted, simple amine groups, such as primary amines, are highly susceptible to oxidation. Substituted amines are less susceptible to such oxidative attack and therefore exhibit increased stability. It is believed substitution of the hydrogen groups on the amine with more complex groups, such as methyl groups, provides protection against oxidation, the more complex groups being less susceptible to substitution. Accordingly, higher degrees of substitution are believed to yield amines of increased stability. Quaternary ammonium groups are particularly preferred for their increased stability.

The polymeric coating material of the present invention is preferably formed by polymerization of one or more allylic or vinylic monomers. Allylic polymers are understood to be polymers derived from monomers comprising at least one allylic group, which is illustrated below in formula (3).

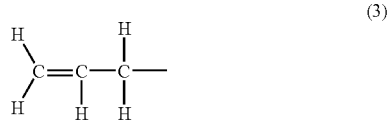

Vinylic polymers are understood to be polymers derived from monomers comprising at least one vinylic group which is illustrated below in formula (4).

Acrylic acid, methacrylic acid, and various esters thereof are examples of vinylic monomers useful in the present invention. Both allylic and vinylic monomers result in formation of non-peptidic polymer backbones and, as a result, exhibit greater resistance to proteolytic degradation than PLL.

In one embodiment of the present invention, a particularly preferred polymer derived from an allylic monomer for use as the polymeric coating material is polydiallyldimethylammonium (PDDA), which is generally available as the chloride salt of the polymer. Like PLL, PDDA is a large polycationic homopolymer that exhibits a strong net positive charge. The strong net positive charge on the PDDA molecule is produced by side chain dimethylated ammonium groups on the residues all along the polymer. The chemical structure of the polymer PDDA is provided below in formula (5), wherein n is an integer representing the number of monomer units in the polymer chain.

PDDA is a particularly stable immobilization agent for use as the polymeric coating material of the present invention. The cationic groups on PDDA are quaternary ammoniums, meaning they are much less susceptible to oxidation as described above. The polymer backbone of PDDA is derived from allylic groups and contain no peptide bonds, such as those found in the PLL molecule. This absence of peptide bonds makes PDDA resistant to attack by proteolytic agents, such as trypsin, that have been proven to break down the PLL polymer chain and reduce immobilization capabilities.

The increased stability of substrates coated with a polymeric coating material comprising PDDA has been substantiated by laboratory testing. In one test, a substrate was coated with a polymeric coating material comprising PDDA, allowed to dry, and rinsed with deionized water. Accelerated stability studies comparing PLL coated substrates against the PDDA coated substrates at 45° C. predicted exceptional performance stability in excess of 15 months. This comparison is further illustrated in Example 2.

In addition, PDDA is advantageous for use in the polymeric coating material of the present invention because of its inherent hydrophilicity. Surprisingly, substrates coated with PDDA exhibit increased hydrophilicity in comparison to substrates coated with the known coating agents, such as PLL. This is an advantageous effect because small aqueous analytical samples will spread more evenly across the substrate coated with PDDA. This allows for a more uniform distribution of the immobilized sample, which facilitates better observation of the immobilized sample.

In another embodiment of the present invention, the polymer used in the polymeric coating material is polyallylamine (PAH), which is generally available as the hydrochloride salt (polyallylamine hydrochloride). As with PDDA, PAH is an allylic polymer having no peptide bonds. The amine group of PAH is not highly substituted, such as with PDDA; however, PAH is still useful as a polymeric coating material according to the present invention. The chemical structure of the polymer PAH is provided below in formula (6), wherein n is an integer representing the number of monomer units in the polymer chain.

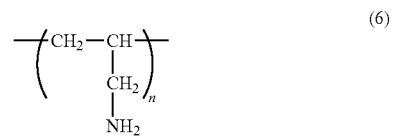

In addition to PDDA and PAH, the polymeric coating material can be a polymer derived from polymerization of one or more various monomers, particularly allylic or vinylic monomers. Accordingly, the polymeric coating material can be a homopolymer, copolymer, or terpolymer. Additionally, the polymeric coating material can be a physical mixture of one or more homopolymers, copolymers, or terpolymers. When the polymeric coating material comprises a homopolymer, the monomers are preferably all cationic monomers; however, when the polymer is a copolymer, terpolymer, or physical polymer mixture, it is not necessary for all monomers to be cationic. In one preferred embodiment, the polymeric coating material comprises a mole percentage of about 5% to about 100% cationic polymer or monomers. More preferably, the polymeric coating material comprises a mole percentage of about 30% to about 100% cationic polymer or monomers, most preferably about 50% to about 100% cationic polymer or monomers.

The cationic monomer used in the polymeric coating material can be cationic in its normal state or can be derivatized from a non-cationic state to a cationic state. Such derivatization can be through any method generally known in the art, such as through addition of an ionic functionality, such as an amine or ammonium group. That is to say, the monomers used to form the polymeric coating material may contain native cationic groups, as in the case of the monomers used to form PDDA and PAH, or can contain side groups that can be derivatized to form cationic side groups.

Preferably, the polymeric coating material is derived from at least one monomer selected from the group consisting of diallyldimethylammonium, allylamine, methylacrylamidopropyltrimethylammonium, acrylamide, acrylic acid, methacryloyloxyethyltrimethylammonium, 4-vinyl-benzyltrimethylammonium, methacrylic acid, hydroxyethylacrylate, methacrylate, methylmethacrylate, hydroxyethylmethacrylate, 4-vinylpyridinium, 4-vinyl-1-methylpyridinium, methyl acrylate, ethyl acrylate, butyl acrylate, 2-ethyl hexyl acrylate, dimethylaminoethylacrylate, dimethylaminoethylacrylate methyl chloride quaternary, dimethylaminopropylacrylamide, dimethylaminopropylacrylamide methyl chloride quaternary, acryloxyethyldimethylbenzyl ammonium, acryloxyethyltrimethyl ammonium, dimethylaminoethylmethacrylate, methacryloxyethyldimethylammonium, methacryloxyethyltrimethylbenzylammonium, ethene, ethyleneimine, propene, styrene, vinyl chloride, isobutylene, trimethyl-2-methacryloylethylammonium, trimethyl-2-methacrylaminopropylammonium, and mixtures thereof.

In another preferred embodiment of the invention, the polymeric coating material comprises a copolymer of a cationic monomer and at least one additional monomer. Preferentially, the polymeric coating material comprises a copolymer of diallyldimethylammonium and at least one additional monomer. Most preferably, the at least one additional monomer comprises a vinylic monomer. In one embodiment, the polymeric coating material comprises a copolymer comprising diallyldimethylammonium and acrylic acid monomer units. In another embodiment, the polymeric coating material comprises a copolymer comprising diallyldimethylammonium and acrylamide monomer units. In another embodiment of the invention, the polymeric coating material comprises a terpolymer comprising diallyldimethylammonium, acrylic acid, and hydroxyethylmethacrylate monomer units.

Preferably, the polymeric coating material according to the present invention is "non-peptidic", meaning the linkages between monomer units are predominately and, preferably substantially, non-peptidic in nature. Preferably, the polymeric coating material comprises no greater than about 25% peptidic monomeric linkages, meaning no more than about 25% of the linkages between monomer units comprise peptide bonds. More preferably, no greater than about 10% of the monomeric linkages are peptidic linkages, and most preferably no greater than about 5% of the monomeric linkages are peptide bonds. In certain preferred embodiments, the polymer coating material is completely free of peptidic linkages.

The polymer used in the polymeric coating material of the present invention is preferably of relatively high molecular weight. High molecular weight polymers are preferred because of the high charge density associated with such high molecular weight. Accordingly, while high molecular weights are preferred, polymers having lesser molecular weights than as described herein would also be useful according to the present invention if the lesser molecular weight polymers exhibited a charge density sufficiently high to be considered equivalent to the charge density of the high molecular weight polymers described herein.

The polymer used in the polymeric coating material preferably has a molecular weight of greater than about 75,000 Da, more preferably greater than about 100,000 Da. In particular embodiments, the polymer has a molecular weight in the range of about 250,000 to about 750,000 Da, most preferably in the range of about 400,000 Da to about 500,000 Da. Unless otherwise noted, molecular weight is expressed herein as weight average molecular weight ($M_w$), which is defined by formula (7) below $$\frac{\sum NiMi^2}{\sum NiMi} \quad (7)$$

wherein Ni is the number of polymer molecules (or the number of moles of those molecules) having molecular weight Mi.

In one preferred embodiment, the polymeric coating material comprises PDDA, as shown above in formula (5), wherein n is an integer between about 500 and 6,000, preferably between about 2,000 and about 5,000, more preferably between about 3,000 and about 4,000. In another preferred embodiment, the polymeric coating material comprises PAH, as shown above in formula (6), wherein n is an integer between about 1,000 and about 15,000, preferably between about 5,000 and about 12,000, more preferably between about 8,000 and about 10,000.

In one aspect of the invention, there is provided a method for preparing a coated substrate that is preferentially adapted for immobilizing a biological sample. Generally, the method comprises providing a substrate having a surface comprising a plurality of anionic groups, contacting the substrate with a composition comprising a solution of anon-peptidic polymeric coating material, as described above, to form a coating of the polymeric coating material on at least a portion of the surface of the substrate, and drying the polymeric coating material coated on the substrate surface.

The substrate used according to the method of the invention can be any substrate comprising a surface having a plurality of anionic groups and exhibiting a net negative charge and that would be useful for immobilizing a sample thereon. Preferably, the substrate is an item useful as a diagnostic tool, an observation tool, an anti-contamination tool, and other similar tools, the use of which would be apparent to one of skill in the art. Preferentially, the substrate used in the method of the invention comprises glass, metals, ceramics, natural or synthetic polymers, natural or synthetic fibrous materials, and mixtures thereof. Specific, non-limiting examples of substrates useful in the method include slides, beads, test tubes, cuvettes, dipsticks, swabs, gauze, and the like.

In one embodiment of the invention, the substrate to be coated with the polymeric coating material is a plate or slide, such as a microscope slide. The slide can comprise any material generally accepted in the art as being useful as such. For example, the slide can be constructed of glass, ceramic, or a polymer material. When glass is used, the glass can be any kind of standard glass comprising primarily silicon dioxide, such as standard soda lime glass. Alternately, the glass can be specialty glass, such as borosilicate glass.

When the slide is comprised of a polymer, it is preferred that the polymer, in its normal state, comprises anionic groups capable of interaction with the cationic groups of the polymeric coating material. In the absence of such groups, however, the polymer can be derivatized to enhance cell adhesion. Examples of polymer useful as slides according to this embodiment of the present invention include, but are not limited to, polystyrene, polyhydroxy methacrylate, polyethylene terephthalate, polytetrafluoroethylene, fluorinated ethylene, and polydimethylsiloxane. The polymer can be a homopolymer, copolymer, terpolymer, or physical polymer mixture.

In a preferred embodiment of the method of the invention, the polymeric coating material is in solution, which can be in an aqueous solution or an organic solution. Any suitable solvent known in the art can be used to solubilize the polymeric coating material, such as deionized water to make an aqueous solution or an alcohol to make an organic solution. The solution can have a concentration of the polymeric coating material ranging from about 0.001% (w/v) to about 50% (w/v). Preferably, the polymeric coating material concentration in the solution is about 0.01% to about 10%, more preferably about 0.05% to about 2%, still more preferably about 0.1% to about 1%, and most preferably about 0.15% to about 0.75%.

Particularly surprising according to the present invention, in certain embodiments, lower concentration solutions can be used to prepare a coated substrate having an immobilization capability superior to a coated substrate prepared using a higher concentration solution. For example, in particular embodiments, solutions having a polymeric coating material concentration of about 0.25% have been shown especially advantageous for preparing a pre-coated substrate according to the invention.

As noted above, the polycationic polymers useful in the invention can exist in a neutral state being coupled with a counterion (for example, chloride in the case of PDDA and hydrochloride in the case of PAH). When in solution, the ions tend to disassociate. Accordingly, the polymer is in its cationic state, ready for use as an immobilizing agent according to the present invention.

The present invention also encompasses facilitating the activation of binding sites on the substrate, thereby increasing the number of anionic sites available for interacting with the cationic groups on the polymeric coating material. Any method known in the art for activation of anionic binding sites on a substrate would be useful according to the present invention.

According to one embodiment of the present invention, the pH of the polymeric coating material can be adjusted. Such adjustment of the pH of the polymeric coating material can be to raise or lower the pH and can take place preceding or following the coating of the substrate with the polymeric coating material. This ability to adjust the pH of the polymeric coating material is particularly advantageous for increasing the number of anionic binding sites on the substrate through deprotonization of the substrate when contacted with the polymeric coating material. Generally, increasing the pH at the substrate surface will promote deprotonization and increase the number of available anionic binding sites.

Preferentially, the pH of the solution comprising the polymeric coating material is adjusted to a preferred pH. In one embodiment, the pH of the solution is at least about 6. In other words, the solution pH is about 8, about 9, about 10, about 11, about 12, about 13, or about 14. In one preferred embodiment, the pH of the solution comprising the polymeric coating material is about 8 to about 14, preferably about 8 to about 10.

After contacting the substrate with the polymeric coating material, the polymeric coating material coated on the substrate is preferably dried prior to further processing or use. Dryness of the polymeric coating material can be evaluated by any method generally known in the art. In one embodiment of the invention, the polymeric coating is at least dried to a point of visual dryness. The visual difference between a wet polymeric material and a dry polymeric material would be easily recognizable to one of skill in the art.

Drying of the polymeric coating material can be achieved by any method generally accepted in the art and can comprise passive drying or active drying (e.g., forced air, such as a fan). The polymeric coating material coated on the substrate can be dried at ambient temperature or at an elevated temperature. Ambient temperature, as used herein, is understood to refer to the temperature of the surrounding environment. In one embodiment, ambient temperature is an average room temperature, generally considered to be in the range of about 20° C. to about 25° C. (about 68° F. to about 77° F.). Of course, temperatures below about 20° C. are not to be excluded by the present invention. In fact, drying could be performed at temperatures as low as about the freezing temperature of the polymeric coating material.

Drying of the polymeric coating material coated on the substrate can also be carried out at an elevated temperature. The temperature can be elevated up to about the temperature wherein further increase would cause degradation of the polymeric coating material. Accordingly, the polymeric coating material coated on the substrate can be at least partially dried at a temperature elevated to about 35° C. to about 120° C. (about 95° F. to about 248° F.), more preferably about 45° C. to about 80° C. (about 113° F. to about 176° F.), most preferably about 50° C. to about 60° C. (122° F. to about 140° F.).

The period of time over which the polymeric coating material coated on the substrate is dried can vary depending upon the temperature and method of drying. Generally, the period of time for drying can vary from about 1 minute to about 1 hour, or longer. For example, when drying of the polymeric coating material coated on the substrate is carried out at ambient temperature, such drying is preferably carried out for a period of time of up to about 1 hour, more preferably for a period of time of about 5 minutes to about 1 hour, and most preferably for a period of time of about 10 minutes to about 30 minutes. Drying at ambient temperature can be continued in excess of 1 hour without detriment to the polymeric coating material.

When drying of the polymeric coating material coated on the substrate is carried out at an elevated temperature, such drying is preferably carried out for a period of time of about 1 minute to about 20 minutes, more preferably for a period of time of about 2 minutes to about 10 minutes. Drying at elevated temperatures can take place for a period of time in excess of about 20 minutes so long as the time and temperature combination would not lead to polymer degradation.

The substrate with the dried polymeric coating material applied thereto is preferentially rinsed, such as with deionized water, prior to use for immobilizing a sample. Such rinsing is useful for removing disassociated counterions as well as excess polymeric coating material that has not ionically interacted with the substrate. Drying the polymeric material coated on the substrate prior to rinsing is preferred since failure to perform the drying step prior to the rinsing step can result in a coated substrate wherein the coating is incomplete (i.e., "patchy"). Rinsing immediately after coating leads to washing away of excessive amounts of the polymeric coating material leaving a coated substrate with limited ability for later immobilization of a sample. Drying the polymeric coating material coated on the substrate prior to rinsing (as described above), however, facilitates maximum ionic interaction between the polymeric coating material and the substrate, which provides a coated substrate having a maximum amount of polymeric coating material applied thereto (i.e., maximum charge density) and therefore having a maximized ability for later immobilization of a sample.

Maximization of immobilization ability is further possible according to the present invention in that there is provided a method for application of the polymeric coating material to the substrate in a controlled manner such that the rinsing step is completely eliminated. Rinsing is generally included in the coating method to remove excess polymeric material that has not been immobilized on the substrate through ionic interactions. This is economically undesirable. First, the rinsing step increases the time necessary to prepare the coated substrates, particularly in mass production, such as with microscope slides. Second, rinsing represents a loss of material. Excess polymeric material applied to the substrate (i.e., polymeric material that does not adhere to the substrate) is lost in the rinse. Again, in mass production, the amount of polymeric material lost in rinsing can add up to a substantial cost.

The present invention solves these problems, however. In one embodiment, the invention provides a method for controlled application of a polymeric material to a substrate. In this method, the volume of polymeric material needed for maximum ionic interaction with the ionic groups on the surface of the substrate is calculated, and only the amount of polymeric material necessary is applied to the substrate. Accordingly, the substrate is coated with the polymeric material, and there is no excess volume present to require a rinsing step. Preferably, the polymeric material is still dried prior to use of the coated substrate for immobilization of a sample.

Another surprising aspect of the present invention heretofore unrecognized in the art is that when the method of the invention specifically excludes subjecting the substrate surface to a cleaning process prior to contacting the substrate with the polymeric coating material, the resulting coated substrate exhibits improved immobilization properties. It is generally accepted in the art that substrates used for immobilizing samples thereon undergo a vigorous cleaning prior to the immobilization step. For example, when the substrate is a microscope slide, common practice is to take the slide, as received from the manufacturer, and wash the slide prior to proceeding with any immobilization steps. Multiple examples of cleaning, or washing, processes are provided by Cras, J. J., et al., *Biosensors & Bioelectronics*, 14 (1999) 683-688.

Cleaning processes to be avoided according to the present invention are processes comprising the use of chemical recognized as useful for removing organic compounds from substrate surfaces. Exemplary of the cleaning processes to be avoided are processes including the use of acids (e.g., hydrochloric acid, sulfiric acid, nitric acid, chromic acid, and chromosulfuric acid), bases (e.g., ammonium hydroxide, sodium hydroxide, and potassium hydroxide), and organic solvents (e.g., methyl alcohol, ethyl alcohol, propyl alcohol, toluene, acetone, methylene chloride, and mineral spirits). Further cleaning processes to be avoided include silanization processes designed to expose silane groups on substrates, such as glass. Processes such as described above (and further described by Cras, J. J., et al.) include a mechanism of action beyond simple rinsing or wiping of a substrate surface. Accordingly, process steps, such as rinsing a substrate with deionized water or wiping the surface of a substrate with a cloth, are not excluded according to the invention. In other words, the present invention encompasses processes wherein a substrate is wiped free of dust or rinsed with water prior to coating with the non-peptidic polymeric material.

Cleaning processes, such as described above, are time consuming and can include the use of toxic chemicals. The method of the present invention, therefore, is particularly useful in that such cleaning steps are completely excluded in preferred embodiments. Accordingly, a microscope slide, for example, can be used as received from the manufacturer without including any cleaning steps. In other words, in the method of the invention, the method excludes subjecting the substrate to a cleaning process prior to contacting the substrate with the non-peptidic polymeric coating material.

In another aspect of the invention, there is provided a pre-coated substrate particularly useful for immobilizing a biological sample thereon. In one embodiment, the pre-coated substrate is prepared according to the method described above.

A pre-coated substrate according to the invention utilizing the polymeric coating material described herein is advantageous in that even when the coating layer of the non-peptidic polymeric coating material is relatively thin, the pre-coated substrate is still useful and effective for immobilizing a biological sample. Of course, the effectiveness of the coating is not limited to such relatively thin coatings, and the polymeric coating material is also effective with relatively thick coatings. The ability to prepare a per-coated substrate according to the invention, however, is particularly advantageous in terms of cost of preparation of such slides. In other words, the ability to prepare substrates for immobilizing a sample thereon using only a thin coating of the polymeric coating material is economical in that a reduced amount of the polymeric material can be used.

The polymeric coating material, when coated on a substrate, can have a thickness of about 0.005 μm to about 500 μm. Preferably, the polymeric coating material has a coating thickness of about 0.5 μm to about 100 μm, more preferably about 1 μm to about 50 μm. Preferably, the polymeric coating material is coated onto the substrate as a single layer, meaning there are no intervening layers of a different material sandwiched between two or more layers of the polymeric coating material of the invention. However, multi-layer coatings are also envisioned by the present invention.

The pre-coated substrate of the present invention is particularly useful not only in terms of increased shelf-life, but also in terms of ability to immobilize an increased amount of a biological sample. For example, in one embodiment, the pre-coated substrate of the invention can be characterized as being capable of immobilizing an increased average number of cells per surface area over other previously known pre-coated substrates.

In one particular embodiment, the average number of cells per surface area immobilized on the pre-coated substrate of the present invention is at least about 10% greater than the average number of cells per surface area over the same area of a substrate not coated according to the methods of the present invention that has been contacted with the same cell sample. Preferably, the average number of cells per surface area immobilized on the pre-coated substrate of the present invention is at least about 15% greater than the average number of cells per surface area over the same area of a substrate not coated according to the methods of the present invention, most preferably at least about 20% greater.

The increased cell count of biological material associated with a pre-coated substrate according to the present invention can be determined using various equipment and methods that would be recognized by one of skill in the art. For example, it is well known in the art that a hemacytometer can be used to count cells manually over a representative number of fields of view and thereafter extrapolate a total number of cells per area.

Cell counts can also be obtained through use of computer-controlled, automated equipment, such as the FOCALPOINT™ Cell Profiler automated slide reading system (available from TriPath Imaging, Inc.). The FOCALPOINT™ Cell Profiler uses specific algorithms to limit the number of cells included in the cell count to a population of diagnostically significant value (i.e., counts only actual cells and disregards artifacts). This cell count is accumulated from approximately 950 to 1,000 images taken at high resolution in fields of cells evaluated as highest potential.

Preferably, methods used to obtain cell counts, such as described above, are capable of providing reproducible results and are capable of providing results that can be evaluated in a statistically significant manner. Accordingly, a biological sample applied to a substrate can be processed using standardized equipment such that samples processed using the equipment can be comparatively evaluated. One example of such processing equipment is a PrepStain Slide Processor (available from TriPath Imaging, Inc.). The PrepStain Slide Processor allows for preparation of a slide with a consistently applied volume of a biological sample, such that the area of the slide to which the sample is applied is consistent and reproducible. Such processing is particularly useful for evaluating a biological sample applied to a substrate based on an average cell count per surface area of the substrate.

One particular embodiment of the invention provides a pre-coated substrate adapted for immobilizing a biological sample for analysis. The substrate can be any substrate as described herein that is coated with a non-peptidic polymeric coating material, such as described above. The pre-coated substrate in this embodiment of the invention is characterized in that it is capable of immobilizing an average number of cells per surface area. Such immobilization ability can be evaluated based on immobilization of a standard cell line. For example, the ability of a pre-coated substrate to immobilize cells can be evaluated using human cervical carcinoma cells, commonly known as a SiHa cell line. SiHa cells are readily available, such as from American Type Culture Collection (ATCC) identified by ATCC Number HTB-35.

According to one embodiment of the invention, a pre-coated substrate is provided wherein the pre-coated substrate surface is capable of immobilizing an average number of cells per surface area of at least about 20,000 cells/cm² when the pre-coated substrate is contacted with 1 mL of a suspension of cells from the SiHa cell line. Preferably, the pre-coated substrate surface is capable of immobilizing an average of at least about 21,000 cells/cm² when the pre-coated substrate is contacted with 1 mL of a suspension of cells from the SiHa cell line, more preferably at least about 22,000 cells/cm², most preferably at least about 23,000 cells/cm².

The improved immobilizing ability of the pre-coated substrate according to the present invention can be observed through further analytical methods as well. One method suitable for use in quantifying charge density of the coated substrate would directly measure charge density in terms of charge density per area of coated substrate. Another method would indirectly measure charge density by correlation to another measurable property. For example, the charge density of the polymeric coating material coated on the substrate can be quantified through spectrographic measurement of a dye associated with the coated substrate (e.g., adsorbed thereon).

As previously noted, the ability of a coated substrate for adhering a biological sample (generally being negatively charged) is directly related to the quantity of excess positive charge on the slide surface. When a negatively charged dye is associated with the slide surface, the excess positive charge on the slide surface can be quantified through spectrographic analysis of the dye. It is well known in the art that the absorption of electromagnetic radiation at a given wavelength by a dye is directly proportional to the concentration of the dye. Therefore, given a proportional relationship between the anionic dye and the cationic coating material, a measurement of absorbance of the dye associated with the coating material is a reliable indicator of the quantity of excess positive charge on the surface of the coated substrate. In other words, the greater the charge density, the greater the concentration of the dye adsorbed on the coated substrate, and the greater the dye's absorption of electromagnetic radiation at a given wavelength. Such a measurement technique is described by Tadao Sakai and Akihiko Hirose (*Talanta* 59 (2003) 167-175), which is incorporated herein by reference.

Multiple dyes known in the art are useful in an analytical technique for quantifying the charge density of a polymeric coating material coated on a substrate according to the present invention. A class of dyes particularly useful for quantifying charge density of a coated substrate in the present invention is xanthene dyes, such as eosin and tetraiodofluorescein. A particularly useful dye according to the present invention is Eosin Y (shown below in formula 8) which is, in a neutral aqueous solution, di-anionic. As a di-anionic species, the dye binds to a mono-cationic species in a 1:2 relationship.

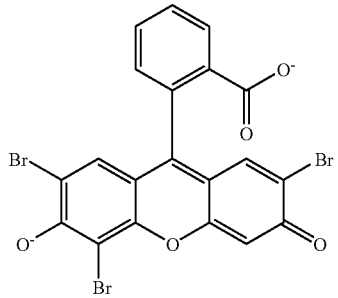

(8)

Eosin Y adsorbed onto a cationic polymer, such as PDDA, has a maximum absorption wavelength ($\lambda_{max}$) of about 542 nm. Therefore, absorption measurements at this wavelength are effective for quantification of excess positive charge on the surface of a coated substrate. Such measurements can be taken on any analytical device known in the art as useful for such measurements, such as a UV-Vis spectrophotometer. An example of the measurement of the charge density of a substrate coated with a polymeric coating material according to the present invention is provided below in Example 4.

A coated substrate according to the present invention coated with a polymeric coating material has an excess of positive charge sites, such excess being of a quantity to effectively bind a biological sample. The polymeric coating material on the coated substrate is effective for binding a biological sample according to the present invention when the polymeric coating material exhibits at least a minimally acceptable charge density. The charge density of a pre-coated substrate prepared according to the present invention, through quantitative measurement, can easily be seen to be much greater than the charge density of a pre-coated substrate that is not prepared according to the present invention. When Eosin Y dye is used in a quantification method as described above, a pre-coated substrate according to the present invention would exhibit an absorbance that is at least twice as great as the absorbance on a substrate not prepared according to the present invention. More preferably, the absorbance exhibited by a substrate according to the present invention is at least about three times greater than the absorbance on a substrate not prepared according to the present invention. Even more preferably, the absorbance exhibited by a substrate according to the present invention is at least about four times greater than the absorbance on a substrate not prepared according to the present invention.

According to one embodiment of the present invention, there is provided a pre-coated glass slide adapted for immobilizing a biological sample for analysis. The glass slide has a plurality of anionic groups, and the slide is coated with a non-peptidic polymeric coating material comprising a plurality of cationic groups. The pre-coated glass slide has a charge density such that when Eosin Y dye is adsorbed on the coated slide and is thereafter subjected to electromagnetic radiation at a wavelength of 542 nm, the dye exhibits an absorbance of at least about 0.05, which is indicative of a minimally acceptable charge density (i.e., excess positive charge) on the polymeric coating material coating the glass slide. Preferably, the absorbance is at least about 0.1. Most preferably, the absorbance is at least about 0.15.

As would be known to one of skill in the art, the choice of substrate could affect the measured absorbance of the dye adsorbed on the coating material used to coat the substrate. Accordingly, if a substrate other than a glass slide was used according to the present invention, absorbance values could vary from the range provided above. Nevertheless, as previously noted, a substrate coated according to the present invention would be would exhibit an absorbance that is at least about two times greater than the absorbance exhibited when the same substrate is coated by a method that is not according to the present invention, preferably at least about three times greater, most preferably at least about four times greater.

The sample for immobilization on the substrate coated with the polymeric coating material can be any sample having anionic groups capable of interacting with the cationic groups of the polymeric coating material and thereby being immobilized thereon. Preferably, the sample comprises a biological component. Examples of biological samples for immobilization on the coated substrate according to the present invention include, but are not limited to, cells, tissue, fluids, nucleic acids, including polynucleotides and oligonucleotides (e.g., DNA, RNA and fragments thereof), polypeptides, and proteins.

In one embodiment according to the present invention, a single layer of the biological sample is immobilized on the substrate coated with the polymeric coating material. The phrase "single layer" is intended to mean that only one layer of material is deposited on, and immobilized on, the coated substrate. Accordingly, no further layers are immobilized in addition to, particularly over, the biological sample, such as would obstruct viewing and hinder analysis of the biological sample immobilized directly on the polymeric coating material on the substrate.

The biological sample can be immobilized on the coated substrate for a variety of uses. Preferentially, the use is a diagnostic use. For example, the biological sample could be immobilized for the purposes of extraction from a greater sample, for additional processing or testing, and for various analytical methods. Specific, non-limiting examples of uses for the coated substrate include, tissue micro-arrays (TMA), cytological micro-arrays (CMA), nucleic acid micro-arrays, and other cytological or histological diagnostics. In addition to such specific uses, the pre-coated substrates of the present invention could also be used for immobilization of various biological samples for manual or automated diagnostic assay kits.

The pre-coated substrate of the invention can be used in a variety of diagnostic methods. For example, the pre-coated substrate could be used to immobilize an antibody that is selective for a particular protein. In another example, the pre-coated substrate could be used to immobilize a reactive substrate, which would be particularly useful for isolating a particular protein that is an enzyme capable of acting on the reactive substrate. Other similar diagnostic uses are also encompassed by the present invention.

In one embodiment of the present invention, there is provided a pre-coated bead. Preferably, the pre-coated bead is adapted for extracting a biological component from a sample. The bead in this embodiment has a surface comprising a plurality of anionic groups capable of interacting with the cationic groups of a non-peptidic polymeric coating material, such as described above. Accordingly, the bead has a non-peptidic polymeric coating material overlaying and ionically attached to the surface of the bead. The coated bead therefore has a plurality of exposed cationic groups for interacting with the anionic groups of the biological component of interest in the sample. The biological component can then be immobilized on the surface of the bead and extracted from the sample.

The pre-coated bead preferentially comprises a material selected from the group consisting of glass, polymers, silicas, metals, metal oxides, and ceramics. In one particularly preferred embodiment, the bead comprises a polymer selected from the group consisting of polystyrene, polyacrylate, polymethacrylate, polyethylene, polypropylene, polyester, polyurethane, polyamide, polycarbonate, polydimethylsiloxane, polydialkylsiloxane, cellulose, derivatives thereof, co-polymers thereof, and combinations thereof.

Pre-coated beads according to the present invention can be used in a variety of extraction and separation methods, such as have been previously described, and as would be readily envisioned by one of skill in the art. For example, the pre-coated beads could be used in various chromatographic separatory methods. Additionally, the pre-coated beads could be inserted into a sample and selectively removed to extract a biological component therefrom.

Of course, the present invention also encompasses multiple other embodiments wherein a pre-coated substrate as described herein can be used in a diagnostic method, and invention is not limited by the present disclosure. For example, embodiments wherein the pre-coated substrate is a microscope slide have previously been described herein.

According to another aspect of the present invention, there is provided a method of analyzing a biological sample. The method generally comprises providing a pre-coated substrate adapted for immobilizing a biological sample, wherein the substrate is coated with a polymeric coating material as described herein, immobilizing the biological sample on the pre-coated substrate, and analyzing the biological sample immobilized on the pre-coated substrate.

In one particular embodiment, the step of analyzing the biological sample immobilized to the pre-coated slide is performed through use of a diagnostic instrument; however, the present invention also contemplates analysis of the immobilized sample by an individual without the aid of additional instrumentation (i.e., through use of the senses alone). Examples of diagnostic instruments useful in the analysis of the immobilized sample according to the present method include, but are not limited to, microscopes (such as light microscopes or electron microscopes), chromatographs, spectrometers, and imaging devices (such as digital cameras, video cameras, and charge-coupled device (CCD) cameras).

The present invention also encompasses various embodiments wherein the pre-coated substrate of the invention has uses other than diagnostic uses, as previously described. For example, in one embodiment, there is provided a device useful for gathering one or more biological contaminants. In this embodiment, as before, the substrate comprises a material having a plurality of anionic groups and is coated with a non-peptidic polymeric coating material. Particularly preferred embodiment in this embodiment, the substrate comprises a fibrous material. The fibrous material can be natural or synthetic and can be woven or non-woven. Non-limiting examples of fibrous materials useful as the biological contaminant gathering device include cotton, cellulose, and polyethylene.

In one preferred embodiment, the biological contaminant gathering device is selected from the group consisting of gauze, towels, and medical drapes. Accordingly, the biological contaminant gathering device can be used in transferring samples, in medical procedures, and in other situations wherein it is useful to collect or gather possible or known biological material to prevent the biological material from contaminating a material or area. For example, the biological contaminant gathering device could be used for holding a slide with a DNA sample thereon. Accordingly, extraneous DNA, such as from the individual handling the slide, is prevented from contaminating the DNA sample on the slide. Similarly, the contaminant gathering device could be used around a surgical site to collect biological material to prevent the material from contaminating the surgical site.

In a particularly preferred embodiment of the invention, the biological contaminant gathering device is a glove, such as a surgical glove. The glove could be comprised of a fibrous material coated with a polymeric coating material as described above. Alternately, the glove could be comprised of a natural or synthetic polymer (e.g., a "rubber" glove).

Further embodiments of the present invention are more distinctly described according to the following experimental examples.

EXPERIMENTAL

The present invention is more fully illustrated by the following examples, which are set forth to illustrate the present invention and are not to be construed as limiting thereof.

Example 1

Pre-Coating Glass Microscope Slide with PDDA

In the preparation of a pre-coated glass microscope slide, a solution of PDDA in deionized water was prepared such that the final concentration of the solution was 1% PDDA (±0.05%) w/v. The pH of the solution was then adjusted to 9.0 (±0.2) through addition of 1N NaOH.

The pH adjusted PDDA solution was placed into a manual slide staining bath. A manual slide staining rack was loaded with glass microscope slides, and the rack with the glass microscope slides was added to the PDDA solution in the bath, with the solution covering the slides up to the frosted edge of the slides. The slides were allowed to rest in the PDDA solution for approximately 10 seconds. The rack was removed from the bath, the slides were removed from the rack, and the slides were placed in an upright, slightly angled position and allowed to dry at ambient temperature. The slides with the PDDA solution applied thereto were allowed to dry to visual dryness then rinsed with deionized water. The rinsed slides were again allowed to dry providing PDDA-coated slides ready for use in analyzing anionic samples.

Example 2

Comparison of PDDA-Coated Microscope Slide with PLL-Coated Microscope Slide

A PDDA solution was prepared and multiple glass microscope slides were coated using the solution according to Example 1. Multiple additional microscope slides were coated similarly using PREPSTAIN™ Slide Coat Reagent (PLL) (available from TriPath Imaging, Inc.).

The PDDA-coated slides and the PLL-coated slides were each separated into two groups. One group of PDDA-coated slides was stored for 16 weeks at ambient temperature. Likewise, one group of PLL-coated slides was stored for 16 weeks at ambient temperature. A second group of PDDA-coated slides, and a second group of PLL-coated slides were stored for 5 weeks at room temperature and were stored for 9 additional weeks at 45° C., for a total of 16 weeks of storage. At the end of the 16 weeks, all four groups of slides were removed from storage for further testing, as described below.

As a comparative in the experimentation, a fresh set of PLL-coated slides was prepared according to the same method previously described for comparison with the Stability Groups.

Slides from each of the five groups described above were subjected to a single pool of cytological material and subsequently stained using the PREPSTAIN™ method. The slides from all five groups were then compared on the basis of the amount of cytological material that adhered to the coated surface.

The PLL coated slides coated were noted as having reduced stability, which decreases with time and temperature. This reduced stability was visibly recognizable from the decreased amount of adhered and stained cytological material present on the PLL coated slides. Slide 1, the control slide, was freshly coated with PLL at the time of evaluation and was not subjected to the 16 week testing. Slide 2, coated with PLL, was allowed to sit at ambient temperature for 16 weeks. A comparison of slide 2 with slide 1 indicated less stained cytological material adhered to slide 2, which indicated a degradation of the polymer coating over the 16-week period. Slide 4, also coated with PLL, sat for 5 weeks at ambient temperature and 9 weeks at 45° C. The polymer degradation in this slide was even more apparent. Visual inspection of slide 4 indicated only minimal cytological material adhered to the slide surface (i.e., practically no visible stained cytological material).

Slide 3 was coated with PDDA and stored at ambient temperature for 16 weeks. Slide 5 was coated with PDDA, stored at ambient temperature for 5 weeks, and then stored at 45° C. for 9 weeks. Both of slides 3 and 5 indicated little to no coating degradation. This was visibly apparent by the complete and even distribution of stained cytological material adhered to the coated slides. Further, in comparison with the freshly coated PLL control slide (slide 1), the PDDA slides, even after sitting for 16 weeks, exhibited deeper staining of the coating, indicating an increased concentration of polymer (and thus cationic binding sites) on the PDDA-coated slides in comparison with the PLL-coated slides.

Example 3

Comparison of Microscope Slides Coated Using Varying Coating Methodologies

Two sets of microscope slides were coated with PDDA according to the method of the present invention and a previously described method. A comparison of the immobilization capabilities of the slides is provided below.

Twelve glass microscope slides were coated with PDDA according to the present invention. Particularly, a 0.25% (w/v) solution of PDDA in deionized water was prepared and pH adjusted using NaOH to a final pH of 9.2. The 12 microscope slides were removed from the packaging as received from the manufacturer and were specifically not subjected to any cleaning process prior to coating with the PDDA solution. Next, the uncleaned slides were manually dipped in the PDDA solution, removed, allowed to dry at ambient conditions to visual dryness, and then rinsed with deionized water to remove any residual PDDA. The rinsed slides were allowed to dry prior to use.

Twelve additional microscope slides were prepared according to known preparation methods for comparison with the PDDA-coated slides of the invention. First, the 12 slides, taken new from the same packaging and manufacturer, were cleaned according to Method 2 disclosed by Cras, J. J., et al., *Biosensors & Bioelectronics,* 14 (1999) 683-688. The cleaned slides were then coated with a 1.0% aqueous PDDA solution according to the method provided by Seyfert, S., et al., *Biomaterials*, 16 (1995) 201-207. Particularly, the cleaned slides were manually dipped in the 1% PDDA solution, removed from the solution, and immediately rinsed to remove any residual PDDA solution (i.e., no drying of the coating was performed prior to rinsing). The rinsed slides were allowed to dry prior to use.

To prepare the cell sample for immobilization of the microscope slides, three bottles of SiHa control cells (from TriPath Imaging, Inc.) were obtained. The SiHa cells used in the experimentation were from a single cell line first described in Friedl, F., *Proc. Soc. Exp. Biol. Med.*, 135 (1970) 543-545. The contents of the three bottles were centrifuged (800 g for 10 minutes) to compact the cells into a pellet. The supernatant was discarded and the cells resuspended in deionized water. The cells were then recompacted into a pellet by centrifugation (800 g for 10 minutes). The supernatant was discarded, and the cells were resuspended into approximately 30 mL deionized water. One mL of the cell suspension was transferred into each of 24 conical tubes, and the samples were processed according to the standard protocol using a TriPath Imaging PREPSTAIN™ Slide Processor instrument (the samples were applied to the slides and stained).

After the slides were stained and coverslipped, the slides were evaluated with a TriPath Imaging FOCALPOINT™ Slide Profiler. The number of cells on each slide was counted by the instrument, and the cell count for each microscope slide was extracted from the instrument's database (cell count being directly proportional to the number of objects registered by the Slide Profiler.

The cell sample on each microscope slide was prepared as a uniform circle having a known diameter of 1.3 cm (13 mm). Accordingly, the sample area on each slide was 1.33 $cm^2$ (132.7 $mm^2$). The number of cells immobilized on each slide is shown below. Table 1 provides the number of cells immobilized on the slides prepared according to the methods of the present invention, and Table 2 provides the number of cells immobilized on the slides prepared according to previously described methods.

TABLE 1

| Slide No. | Cell Count |
| --- | --- |
| 1 | 28,997 |
| 2 | 27,914 |
| 3 | 25,992 |
| 4 | 24,398 |
| 5 | 22,525 |
| 6 | 39,738 |
| 7 | 41,413 |
| 8 | 36,446 |
| 9 | 38,968 |
| 10 | 26,200 |
| 11 | 27,023 |
| 12 | 35,053 |
| Average | 31,222 |

TABLE 2

| Slide No. | Cell Count |
| --- | --- |
| 13 | 25,521 |
| 14 | 24,361 |
| 15 | 24,712 |
| 16 | 25,086 |
| 17 | 26,011 |
| 18 | 25,419 |

TABLE 2-continued

| Slide No. | Cell Count |
| --- | --- |
| 19 | 23,528 |
| 20 | 29,788 |
| 21 | 28,230 |
| 22 | 22,035 |
| 23 | 25,843 |
| 24 | 24,146 |
| Average | 25,390 |

Comparison of the cells counts provided above in Table 1 and Table 2 using Student's t-distribution reveals a significance level of less than 0.005. Accordingly, the cell counts illustrate with statistical significance that the PDDA coated slides prepared according to the present invention immobilize a greater average number of cells than PDDA coated slides prepared according to previously known methods. In particular, the PDDA coated slides of the invention immobilized an average number of cells 22.97% greater than the average number of cells immobilized on the PDDA coated slides prepared according to the previously known methods.

As noted above, the cell sample area on each slide was 1.33 $cm^2$ (132.7 $mm^2$). Accordingly, it is possible to calculate the average number of cells immobilized on a given surface area. With the slides prepared according to the present invention, the average number of cells per surface area immobilized was 23,475 cells/$cm^2$ (235.2 cells/$mm^2$). By contrast, the slides prepared according to previously known methods had an average number of cells per surface area immobilized of only 19,090 cells/$cm^2$ (191.3 cells/$mm^2$).

Example 4

Analysis of Slides Coated with PDDA by UV Absorption of Adsorbed Eosin Y Dye

Fifteen ESCO microscope slides (catalog number 2951) were obtained. Three slides were set aside for use as control slides. The remaining twelve slides were divided into four groups of three slides each. Group 1 slides were coated with a 1% solution of PDDA at a pH of approximately 9.2. The coated slides were allowed to dry for 1 hour, were rinsed with deionized water, and allowed to dry for an additional 1 hour. Group 2 slides were coated with a 1% solution of PDDA at a pH of approximately 9.2. The coated slides were immediately rinsed with deionized water (no drying of the PDDA coating), and the rinsed slides were allowed to dry for 1 hour. Group 3 slides were coated with a 1% solution of PDDA at a pH of approximately 5.3. The coated slides were allowed to dry for 1 hour, were rinsed with deionized water, and allowed to dry for an additional 1 hour. Group 4 slides were coated with a 1% solution of PDDA at a pH of approximately 5.3. The coated slides were immediately rinsed with deionized water (no drying of the PDDA coating), and the rinsed slides were allowed to dry for 1 hour. Group 5 slides (the control slides) were not coated.

All slides in the above 5 groups were prepared for treatment by placing each slide into a Hettich microscope slide-holder base and positioning a Hettich settling chamber on the slides to isolate a portion of the slide. The isolated portion of the surface of each slide was treated with 200 µL of a 5% w/v Eosin Y solution in deionized water for 1 minute. The dye solution was removed with vacuum suction, and each slide was treated twice with 2.5 mL of deionized water, allowing each rinse to stand for 1 minute before removing with vacuum suction. Each slide was then treated twice with 2.5 mL isopropanol, allowing each rinse to stand for 1 minute before removing with vacuum suction. Each slide was then removed from the slide holder and allowed to dry for at least 10 minutes. Each slide treated with the dye had a circular stained portion having an area of about 240 mm², the center of the circular stained portion being approximately 17.5 mm from the unfrosted short end of the slide.

Spectrographic analysis was performed using a UV-Vis spectrophotometer as 542 nm. The instrument was zeroed using a plain, untreated, uncoated glass slide. The measured absorbance for each slide (provided below in Table 6) indicated a significant difference between slides coated with no drying of the polymeric coating prior to rinsing and those coated by the method of the present invention. Eosin Y adsorption onto the positively-charged surfaces of the PDDA-coated slides was much greater on the slides which were allowed to dry at ambient temperature for about 1 hour prior to being rinsed with deionized water.

TABLE 3

| Method of Slide Treatment | Average Absorbance |
| --- | --- |
| Group 1 - PDDA coated (1%), pH 9.2, dried prior to rinsing | 0.158 |
| Group 2 - PDDA coated (1%), pH 9.2, not dried prior to rinsing | 0.037 |
| Group 3 - PDDA coated (1%), pH 5.3, dried prior to rinsing | 0.109 |
| Group 4 - PDDA coated (1%), pH 5.3, not dried prior to rinsing | 0.023 |
| Group 5 - Uncoated | 0.002 |

A direct comparison of the slides coated without drying (Group 2) and the slides coated according to the methods of the present invention (Group 1), both at pH 9.2, indicates that the excess positive charge was about 4.3 (±0.8) times greater on the slides prepared according to the present invention. Similarly, a direct comparison of the slides coated without drying (Group 4) and the slides coated according to the methods of the present invention (Group 3), both at pH 5.3, indicates that the excess positive charge was about 4.7 (±3.0) times greater on the slides prepared according to the present invention. The contribution of the glass itself to the adsorption of Eosin Y dye is negligible, as indicated by the near-zero absorption values for the uncoated slides (control slides). The adsorption of Eosin Y dye can therefore be attributed solely to the positive charges carried by the PDDA coated on the slides.

Many modifications and other embodiments of the inventions set forth herein will come to mind to one skilled in the art to which these inventions pertain having the benefit of the teachings presented in the foregoing description. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method for preparing a coated substrate adapted for immobilizing a biological sample, said method comprising:
    providing a glass substrate having a surface comprising a plurality of anionic groups;
    contacting the substrate with a composition comprising a solution of a non-peptidic, quaternary ammonium polymeric material comprising at least one monomer selected from the group consisting of diallyldimethylammonium, methylacrylamidopropyltrimethylammonium, methacryloyloxyethyltrimethylammonium, 4-vinyl-benzyltrimethylammonium, acryloxyethyldimethylbenzyl ammonium, acryloxyethyltrimethyl ammonium, methacryloxyethyldimethylammonium, methacryloxyethyltrimethylbenzylammonium, trimethyl-2-methacryloylethylammonium, trimethyl-2-methacrylaminopropylammonium, and mixtures thereof, said quaternary ammonium polymeric material present in a concentration of about 0.01% (w/v) to about 10.0% (w/v) in solution, the solution having a pH of about 8 to about 14, to form a coating of a single layer of the non-peptidic, quaternary ammonium polymeric material on at least a portion of the surface of the substrate with no intervening layers of a different coating material sandwiched between two or more layers of the non-peptidic, quaternary ammonium polymeric coating material and with no further layers of any material coated over said layer of the non-peptidic, quaternary ammonium polymeric material; wherein the non-peptidic, quaternary ammonium polymeric coating material has an average molecular weight of about 400,000 Da to about 500,000 Da, and
    drying the coating of the non-peptidic, quaternary ammonium polymeric material.

2. The method according to claim 1, wherein said step of drying the coated substrate is carried out at ambient temperature.

3. The method according to claim 2, wherein said step of drying the coated substrate is carried out for a period of time of about 5 minutes to about 1 hour.

4. The method according to claim 1, wherein said step of drying the coated substrate is carried out at a temperature of about 35° C. to about 120° C.

5. The method according to claim 4, wherein said step of drying the coated substrate is carried out for a period of time of about 1 minute to about 20 minutes.

6. The method according to claim 1, wherein the substrate is selected from the group consisting of slides, plates, beads, test tubes, cuvettes, and dipsticks.

7. The method according to claim 1, wherein the substrate is a microscope slide.

8. The method according to claim 1, wherein the non-peptidic, quaternary ammonium polymeric material comprises polydiallyldimethylammonium.

9. The method according to claim 1, wherein the non-peptidic, quaternary ammonium polymeric material comprises a copolymer of diallyldimethylammonium and at least one additional monomer.

10. The method of claim 1, wherein the non-peptidic, quaternary ammonium polymeric coating is present in solution at a concentration of about 0.15% (w/v) to about 0.75% (w/v).

11. The method according to claim 1, wherein the substrate surface has not been subjected to a cleaning process prior to contacting the substrate with the solution of the non-peptidic, quaternary ammonium polymeric material.

12. The method according to claim 11, wherein the substrate surface has not been subjected to a cleaning process incorporating an acid, a base, or an organic solvent prior to contacting the substrate with the solution of the non-peptidic, quaternary ammonium polymeric material.

13. The method according to claim 1, wherein the substrate surface has not be subjected to a silanization process prior to contacting the substrate with the solution of the non-peptidic, quaternary ammonium polymeric material.

14. The method according to claim 1, further comprising rinsing the substrate having the dried coating of the non-peptidic, quaternary ammonium polymeric material thereon.

15. A method for preparing a microscope slide adapted for immobilizing a biological sample, said method comprising:
providing a previously manufactured microscope slide having a surface comprising a plurality of anionic groups;
contacting the surface of the microscope slide with a composition comprising a solution of a non-peptidic, quaternary ammonium polymeric material present in a concentration of about 0.01% (w/v) to about 10.0% (w/v) in solution, the solution having a pH of about 8 to about 14, to form a coating of the non-peptidic, quaternary ammonium polymeric material on at least a portion of the surface of the microscope slide with no intervening layers of a different coating material sandwiched between two or more layers of the non-peptidic, quaternary ammonium polymeric coating material and with no further layers of any material coated over said layer of the non-peptidic, quaternary ammonium polymeric material; wherein the non-peptidic, quaternary ammonium polymeric coating material has an average molecular weight of about 400,000 Da to about 500,000 Da,
drying the coating of the non-peptidic, quaternary ammonium polymeric material; and
rinsing the microscope slide having the dried coating of the non-peptidic, quaternary ammonium polymeric material thereon;
wherein the microscope slide surface has not been subjected to a cleaning process after receipt from the manufacturer and prior to contacting the microscope slide surface with the solution of the non-peptidic, quaternary ammonium polymeric material.

16. The method according to claim 15, wherein the slide comprises a material selected from the group consisting of glass, ceramics, and polymer materials.

17. The method according to claim 16, wherein the slide comprises a polymer selected from the group consisting of polystyrene, polyhydroxy methacrylate, polyethylene terephthalate, polytetrafluoroethylene, fluorinated ethylene, polydimethylsiloxane, copolymers or terpolymers thereof, and combinations thereof.

18. The method according to claim 15, wherein the non-peptidic, quaternary ammonium polymeric material comprises at least one monomer selected from the group consisting of diallyldimethylammonium, methylacrylamidopropyltrimethylammonium, methacryloyloxyethyltrimethylammonium, 4-vinyl-benzyltrimethylammonium, acryloxyethyldimethylbenzyl ammonium, acryloxyethyltrimethyl ammonium, methacryloxyethyldimethylammonium, methacryloxyethyltrimethylbenzylammonium, trimethyl-2-methacryloylethylammonium, trimethyl-2-methacrylaminopropylammonium, and mixtures thereof.

19. The method according to claim 15, wherein the non-peptidic, quaternary ammonium polymeric material comprises a polymer selected from the group of allylic polymers.

20. The method according to claim 15, wherein the non-peptidic, quaternary ammonium polymeric material comprises polydiallyldimethylammonium.

21. A method for preparing a microscope slide adapted for immobilizing a biological sample, said method comprising:
providing a previously manufactured microscope slide having a surface comprising a plurality of anionic groups; and
contacting the surface of the microscope slide with a composition comprising a solution of a non-peptidic, quaternary ammonium polymeric present in a concentration of about 0.01% (w/v) to about 10.0% (w/v) in solution, the solution having a pH of about 8 to about 14, to form a coating of the non-peptidic, quaternary ammonium polymeric material on at least a portion of the surface of the microscope slide with no intervening layers of a different coating material sandwiched between two or more layers of the non-peptidic, quaternary ammonium polymeric coating material and with no further layers of any material coated over said layer of the non-peptidic, quaternary ammonium polymeric material, wherein the non-peptidic, quaternary ammonium polymeric coating material has an average molecular weight of about 400,000 Da to about 500,000 Da.

22. The method according to claim 21, wherein the slide comprises a material selected from the group consisting of glass, ceramics, and polymer materials.

23. The method according to claim 22, wherein the slide comprises a polymer selected from the group consisting of polystyrene, polyhydroxy methacrylate, polyethylene terephthalate, polytetrafluoroethylene, fluorinated ethylene, polydimethylsiloxane, copolymers or terpolymers thereof, and combinations thereof.

24. The method according to claim 21, wherein the non-peptidic, quaternary ammonium polymeric material comprises at least one monomer selected from the group consisting of diallyldimethylammonium, methylacrylamidopropyltrimethylammonium, methacryloyloxyethyltrimethylammonium, 4-vinyl-benzyltrimethylammonium, acryloxyethyldimethylbenzyl ammonium, acryloxyethyltrimethyl ammonium, methacryloxyethyldimethylammonium, methacryloxyethyltrimethylbenzylammonium, trimethyl-2-methacryloylethylammonium, trimethyl-2-methacrylaminopropylammonium, and mixtures thereof.

25. The method according to claim 21, wherein the non-peptidic, quaternary ammonium polymeric material comprises a polymer selected from the group of allylic polymers.

26. The method according to claim 21, wherein the non-peptidic, quaternary ammonium polymeric material comprises polydiallyldimethylammonium.

27. A method for preparing a microscope slide adapted for immobilizing a biological sample, said method comprising:
providing a previously manufactured microscope slide having a surface comprising a plurality of anionic groups; and
contacting the surface of the microscope slide with a composition comprising a solution of polydiallyldimethylammonium present in a concentration of about 0.01% (w/v) to about 10.0% (w/v) in solution, the solution having a pH of about 8 to about 14, to form a coating of the polydiallyldimethylammonium on at least a portion of the surface of the microscope slide with no intervening layers of a different coating material sandwiched between two or more layers of the polydiallyldimethylammonium and with no further layers of any material coated over said layer of the polydiallyldimethylammonium, wherein the non-peptidic, quaternary ammonium polymeric coating material has an average molecular weight of about 400,000 Da to about 500,000 Da.

28. The method according to claim 27, wherein the slide comprises a material selected from the group consisting of glass, ceramics, and polymer materials.

29. The method according to claim 28, wherein the slide comprises a polymer selected from the group consisting of polystyrene, polyhydroxy methacrylate, polyethylene terephthalate, polytetrafluoroethylene, fluorinated ethylene, polydimethylsiloxane, copolymers or terpolymers thereof, and combinations thereof.

30. A method for preparing a coated substrate adapted for immobilizing a biological sample, said method comprising:
providing a glass substrate having a surface comprising a plurality of anionic groups; and
contacting the surface of the glass substrate with a composition comprising a solution of a non-peptidic, quaternary ammonium polymeric material present in a concentration of about 0.01% (w/v) to about 10.0% (w/v) in solution, the solution having a pH of about 8 to about 14, to form a coating of the non-peptidic, quaternary ammonium polymeric material on at least a portion of the surface of the glass substrate microscope slide with no intervening layers of a different coating material sandwiched between two or more layers of the non-peptidic, quaternary ammonium polymeric material, and with no further layers of any material coated over said layer of the non-peptidic, quaternary ammonium polymeric material, wherein the non-peptidic, quaternary ammonium polymeric coating material has an average molecular weight of about 400,000 Da to about 500,000 Da.

31. The method according to claim 30, wherein the substrate is selected from the group consisting of slides, plates, beads, test tubes, cuvettes, and dipsticks.

32. The method of claim 30, wherein said concentration is about 0.25% (w/v).

33. The method of claim 30, wherein said concentration is about 0.15% (w/v) to about 0.75% (w/v).

34. The method of claim 1, wherein said concentration is about 0.25% (w/v).

35. The method of claim 15, wherein said concentration is about 0.25% (w/v).

36. The method of claim 15, wherein said concentration is about 0.15% (w/v) to about 0.75% (w/v).

37. The method of claim 21, wherein said concentration is about 0.25% (w/v).

38. The method of claim 21, wherein said concentration is about 0.15% (w/v) to about 0.75% (w/v).

39. The method of claim 27, wherein said concentration is about 0.25% (w/v).

40. The method of claim 27, wherein said concentration is about 0.15% (w/v) to about 0.75% (w/v).

41. A method for preparing a coated substrate adapted for immobilizing a biological sample, said method comprising:
providing a glass substrate having a surface comprising a plurality of anionic groups;
contacting the substrate with a composition comprising a solution of a non-peptidic, quaternary ammonium polymeric material comprising at least one monomer selected from the group consisting of diallyldimethylammonium, methylacrylamidopropyltrimethylammonium, methacryloyloxyethyltrimethylammonium, 4-vinyl-benzyltrimethylammonium, acryloxyethyldimethylbenzyl ammonium, acryloxyethyltrimethyl ammonium, methacryloxyethyldimethylammonium, methacryloxyethyltrimethylbenzylammonium, trimethyl-2-methacryloylethylammonium, trimethyl-2-methacrylaminopropylammonium, and mixtures thereof, said quaternary ammonium polymeric material present in a concentration of about 0.15% (w/v) to about 0.75% (w/v) in solution, the solution having a pH of about 8 to about 14, to form a coating of a single layer of the non-peptidic, quaternary ammonium polymeric material on at least a portion of the surface of the substrate with no intervening layers of a different coating material sandwiched between two or more layers of the non-peptidic, quaternary ammonium polymeric coating material and with no further layers of any material coated over said layer of the non-peptidic, quaternary ammonium polymeric material and
drying the coating of the non-peptidic, quaternary ammonium polymeric material.

* * * * *